United States Patent
Uchida et al.

(10) Patent No.: US 7,872,058 B2
(45) Date of Patent: *Jan. 18, 2011

(54) PHOTOPOLYMERIZABLE DENTAL COMPOSITION WITH LESS CHANGE IN COLOR TONE BEFORE AND AFTER CURING

(75) Inventors: Jun Uchida, Kyoto (JP); Mitsuharu Mizuno, Kyoto (JP); Mitsuji Teramae, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 7 days.

This patent is subject to a terminal disclaimer.

(21) Appl. No.: 12/379,926

(22) Filed: Mar. 4, 2009

(65) Prior Publication Data

US 2009/0227700 A1 Sep. 10, 2009

(30) Foreign Application Priority Data

Mar. 4, 2008 (JP) .............................. 2008-052962

(51) Int. Cl.
*C08F 2/50* (2006.01)

(52) U.S. Cl. .............................. 522/64; 522/12; 522/18; 522/28; 522/38; 522/48; 522/71; 522/74; 522/81; 522/82; 522/83; 522/100; 522/114; 522/113; 522/120; 523/105; 523/109; 523/113; 523/115; 523/116; 523/120; 523/118

(58) Field of Classification Search ................... 522/12, 522/18, 28, 38, 48, 64, 82, 83, 71, 74, 100, 522/101, 113, 114, 120, 121; 523/105, 109, 523/113, 115, 116, 118, 120, 300
See application file for complete search history.

(56) References Cited

U.S. PATENT DOCUMENTS

| 6,730,715 B2 * | 5/2004 | Jia | ............................. 523/115 |
| 2003/0083400 A1 * | 5/2003 | Jia | ............................. 523/116 |

* cited by examiner

*Primary Examiner*—Sanza L McClendon
(74) *Attorney, Agent, or Firm*—Wenderoth, Lind & Ponack, L.L.P.

(57) ABSTRACT

An object of the present invention is to provide a photopolymerizable dental composition which causes less change in a color tone before and after curing and exhibits excellent photopolymerizability to irradiation in a wide wavelength range, and has also excellent thin-layer surface curability, and to provide a photopolymerization initiator used therefor.

Disclosed is a visible light-polymerizable dental composition which does not substantially contain an amine compound as a photosensitizer, comprising 0.01 to 10 parts by weight of a (bis)acylphosphine oxide compound, 0.01 to 10 parts by weight of an α-diketone compound and 100 parts by weight of a polymerizable monomer.

23 Claims, 1 Drawing Sheet

PHOTOPOLYMERIZABLE DENTAL COMPOSITION WITH LESS CHANGE IN COLOR TONE BEFORE AND AFTER CURING

BACKGROUND OF THE INVENTION

1. Field of the Invention

The present invention relates to a photopolymerizable dental composition which is cured by irradiation with visible light, and a photopolymerization initiator used therefor. More particularly, the present invention relates to a dental composition which causes less change of a color tone before and after curing, and also can be cured by irradiation with light in a wide wavelength range. The composition of the present invention is used for fillers, adhesives, surface coating materials, restorative materials for dental crowns, cements, etc.

2. Description of the Related Art

Current dental treatments view aesthetic qualities as one of the most important elements. There is a strong requirement for the characteristics of dental materials to be such that the color of restorations resembles that of a natural tooth, and has a beautiful white color.

In actual treatment, a color tone is determined by comparing a color tone of the natural tooth of the patient with that of materials such as fillers. However, materials comprising a combination of a conventionally used visible light-photopolymerization catalyst and a polymerizable monomer displayed inferior aesthetic qualities since a color tone varies before and after curing, resulting in poor compatibility with a color tone after mounting in the oral cavity.

In the dental field, a visible light-polymerizable resin has been widely used. The disclosure of UK Patent No. GB1408265 resulted in broad application of a photopolymerization initiator therefor including a hydrogen abstracting initiator comprising an a-diketone compound and an amine compound, such as camphorquinone having a maximum absorption wavelength of 470 nm. However, a photopolymerization initiator comprising an a-diketone compound and an amine compound has problems such as drastic yellowing and change of a color tone of the cured article associated with the amine compound, and poor thin-layer surface curability.

(Bis)acylphosphine oxide compounds disclosed in U.S. Pat. Nos. 4,265,723, 4,298,738, 4,792,632 and 5,965,776 show excellent photopolymerizability in an ultraviolet or near ultraviolet range and are therefore widely used in the photopolymerization industry field. The (bis)acylphosphine oxide compounds are less likely to cause yellowing of the cured article and also display excellent internal curability. Therefore, (bis)acylphosphine oxide compounds are used for photocuring of transparent thick films and materials containing pigments having a large hiding power, and have also found recent application in the dental field. However, since the absorption wavelength range of (bis)acylphosphine oxide compounds is on the short wavelength side of visible light, the (bis)acylphosphine oxide compounds have the drawback that curing occurs when a photopolymerization device with a light source such as a halogen lamp is used, while curing does not occur when the device having a narrow photoradiation wavelength range such as blue LED is used. A dental material using (bis)acylphosphine oxide compounds has a drawback that it has a colorless color tone before curing but yellowing occurs after curing.

Japanese Unexamined Patent Publication (Kokai) No. 2000-16910 reports that a curable composition containing a (bis)acylphosphine oxide compound and an amine compound displays physical properties of cured articles such as a high strength and a low amount of an unpolymerized material on the surface. However, this initiator has a problem that severe change in a color tone of the cured article is caused by the amine compound.

Japanese Patent No. 3,442,776 proposes a visible light-polymerizable adhesive comprising an a-diketone compound, a (bis)acylphosphine oxide compound, an amine compound and a polymerizable monomer. However, a curable composition using an amine compound as the photoinitiator has a problem that severe change in a color tone of the cured article occurs and a usable life drastically decreases.

Japanese Patent No. 2,629,060 reports a photopolymerizable dental surface coating material comprising dipentaerythritol hexaacrylate and a (bis)acylphosphine oxide compound. This patent reports that the photopolymerizable dental surface coating material is excellent in thin layer surface curability since it contains dipentaerythritol hexaacrylate and a (bis)acylphosphine oxide compound. However, there is a problem that curing caused by dipentaerythritol hexaacrylate and the (bis)acylphosphine oxide compound causes browning of the cured article.

Japanese Unexamined Patent Publication (Kokai) No. 6-55654 proposes a photocurable dental crown material comprising polyfunctional (meth)acrylate, an alumina filler and acylphosphine oxide. Although discoloration of the material is improved by this invention, surface curability of a thin-layer is not taken into consideration.

SUMMARY OF THE INVENTION

Thus, the present inventors have intensively studied photopolymerization initiators which cause less change in a color tone before and after curing. As a result, surprisingly, we have found that a visible light-polymerizable dental composition using, as a photosensitizer, a visible light-polymerizable initiator which does not substantially contain an amine compound and contains an a-diketone compound and a (bis)acylphosphine oxide compound has a feature that it causes less change in a color tone before and after curing, and also exhibits excellent photopolymerizability when irradiated with a dental irradiation device in a wide wavelength range, thereby imparting excellent physical properties. Thus, the present invention has been completed. It was also found that improved thin layer surface curability effects are exerted in this composition.

That is, the present invention provides:

[1] A visible light-polymerizable dental composition which does not substantially contain an amine compound as a photosensitizer, comprising 0.01 to 10 parts by weight of a (bis)acylphosphine oxide compound, 0.01 to 10 parts by weight of an a-diketone compound and 100 parts by weight of a polymerizable monomer;

[2] The visible light-polymerizable dental composition according to above-described [1], wherein the (bis)acylphosphine oxide compound is 2,4,6-trimethylbenzoyldiphenylphosphine oxide;

[3] The visible light-polymerizable dental composition according to above-described [1] or [2], wherein the a-diketone compound is camphorquinone;

[4] The visible light-polymerizable dental composition according to any one of above-described [1] to [3], which contains, as the polymerizable monomer, dipentaerythritol hexaacrylate;

[5] The visible light-polymerizable dental composition according to any one of above-described [1] to [4], which contains, as the polymerizable monomer, a compound represented by the general formula (I):

[Chemical Formula 1]

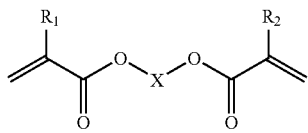

(I)

wherein $R_1$ and $R_2$ each independently represent hydrogen or a methyl group, and X represents a repeating unit composed of one or more kinds of alkylene oxide groups having 2 to 10 carbon atoms and/or derivative groups thereof and the repeating unit number n=5 to 50;

[6] The visible light-polymerizable dental composition according to above-described [5], wherein X in the general formula (I) is a repeating unit composed only of an ethylene oxide group and the repeating unit number n=9 to 23;

[7] The visible light-polymerizable dental composition according to above-described [5] or [6], which contains the polymerizable monomer represented by the general formula (I) in the amount of 5 to 90 parts by weight based on the entire amount of the polymerizable monomer;

[8] The visible light-polymerizable dental composition according to any one of above-described [1] to [7], which further contains 0.1 to 90 parts by weight of at least one kind of an inorganic or organic filler;

[9] The visible light-polymerizable dental composition according to any one of above-described [1] to [8], which is thixotropic in that a ratio of a minimum value to a maximum value of the viscosity at a frequency of 7 to 1 Hz is 1.1 or more and the viscosity takes a value from 2 to 8 Pa·s at a frequency sweep of 7 to 1 Hz measured at an initial stress of 1.00 E+1 Pa in the measurement of plate-on-plate viscosity at 23° C. (gap: 0.500 mm).

The photopolymerizable dental composition which is cured by irradiating with visible light and a photopolymerization initiator used therefor of the present invention cause less change in a color tone before and after curing, and also can be cured by light of a wide wavelength range. The photopolymerization initiator and the dental composition of the present invention are used for fillers, adhesives, surface coating materials, restorative materials for dental crowns, cements, etc.

DETAILED DESCRIPTION OF THE INVENTION

Figure 1:
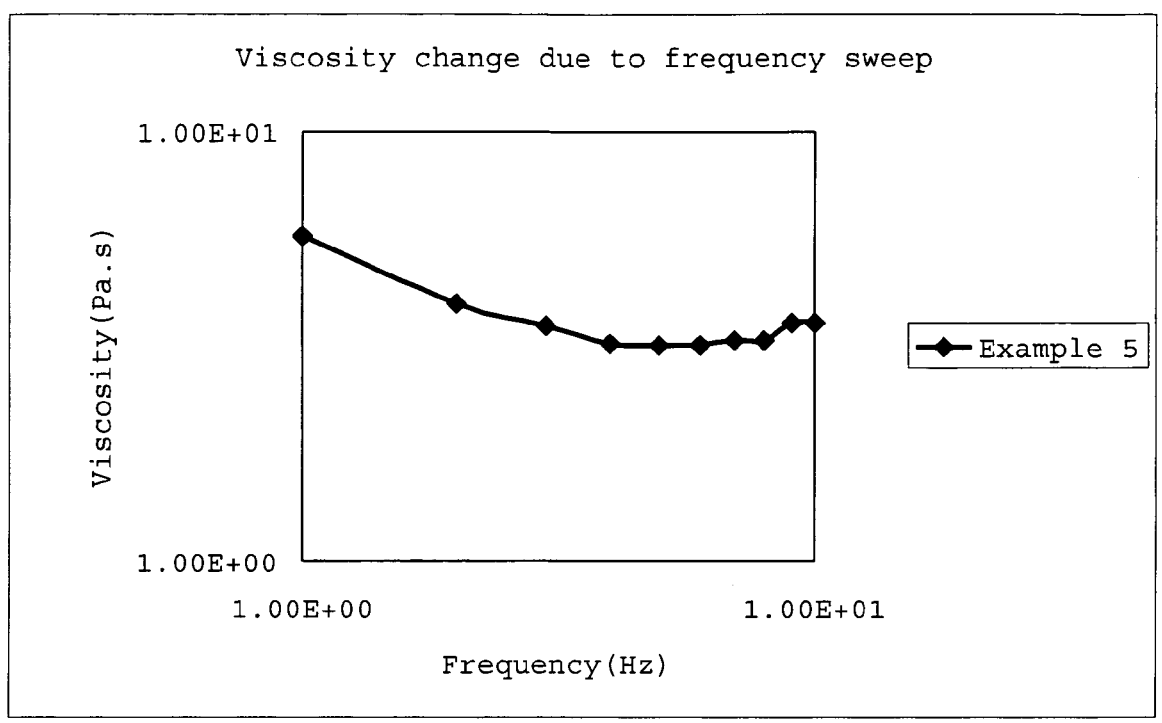
FIG. 1 is a graph showing logarithmically plotted measurement results of the viscosity of a composition of the present invention.

The present invention will now be described in detail.

The dental composition and the photopolymerization initiator used therefor of the present invention have a feature that they do not substantially contain, as a photosensitizer, an amine mine compound. As used herein, "which does not substantially contain, as a photosensitizer, an amine compound" means that an amine compound as a photosensitizer is not actively contained in the composition, and an amine compound derived from another component material passively contained is not included in this definition. Specifically, it is permitted that the amine compound is contained in the photopolymerization initiator of the present invention in the amount of 0 to 1 part by weight and in the visible light-polymerizable dental composition in the amount of 0 to 0.1 part by weight.

When the amine compound as the photosensitizer (stabilizer, reducing agent) is added to the dental composition, unpleasant odor peculiar to an amine gives the users an unpleasant feeling. Since the amine compound may cause browning of the color tone after curing, a fatal discoloration from an aesthetical point of view arises.

The present inventors have found a photopolymerization initiator, which causes less change in a color tone before and after curing and is also excellent in thin-layer surface curability, without using photosensitizers such as these amine compounds. Therefore, the dental composition containing the photopolymerization initiator of the present invention is excellent in view of discoloration, odor and storage stability when compared with the dental materials containing an amine compound disclosed in Japanese Patent No. 3,442,776.

In the field of dental materials, a (bis)acylphosphine oxide compound is used as a photopolymerization initiator having excellent curing characteristics. However, since an absorption wavelength range of the (bis)acylphosphine oxide compound is on the short wavelength side of visible light, the (bis)acylphosphine oxide compound has a drawback that curing occurs when a photopolymerization device with a light source such as a halogen lamp is used, while curing does not occur when the device having a narrow photoradiation wavelength range such as blue LED is used. A dental material using the (bis)acylphosphine oxide compound has also a drawback that it has a colorless color tone before curing but yellowing occurs after curing.

Conventionally, an a-diketone compound is also widely used as the photopolymerization initiator. The a-diketone compound corresponds to the comparatively wide wavelength range of 400 to 500 nm (center: around 470 nm), but has a drawback that the composition before curing becomes yellowish. In order to impart sufficient curing characteristics to the dental material, it was indispensable to use it in combination with the photosensitizer such as an amine compound.

Thus, the present inventors have found that the use of a (bis)acylphosphine oxide compound, a photopolymerization initiator, and an a-diketone compound in combination exert various effects such as improvement in curability in a wide wavelength range, decrease of change in a color tone before and after curing, and improvement in thin-layer surface curability.

Specific examples of the (bis)acylphosphine oxide compound used in the present invention include 2,4,6-trimethylbenzoyldiphenylphosphine oxide, 2,6-dimethoxybenzoyldiphenylphosphine oxide, 2,6-dichlorobenzoyldiphenylphosphine oxide, methyl 2,4,6-trimethylbenzoylphenylphosphinate, 2-methylbenzoyldiphenylphosphine oxide, isopropyl pivaloylphenylphosphinate, bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, etc. Among these compounds, 2,4,6-trimethylbenzoyldiphenylphosphine oxide is particularly preferable in view of curing within a short time, very slight change in a color tone before and after curing, etc.

The amount of the (bis)acylphosphine oxide compound in the dental composition is from 0.01 to 10 parts by weight, preferably from 0.05 to 6 parts by weight, and more preferably from 0.1 to 4.0 parts by weight, based on 100 parts by weight of the polymerizable monomer. When the amount of the (bis)acylphosphine oxide compound is less than 0.01 part by weight, thin-layer curability deteriorates and, conversely, when the amount of the (bis)acylphosphine oxide compound is more than 10 parts by weight, a yellow color tone increases and a usable life decreases, being not preferable.

Examples of the a-diketone compound used in the present invention include diacetil, benzil, 4,4'-dimethoxybenzil, 4,4'-dimethoxybenzil, 4,4'-oxybenzil, 4,4'-chlorobenzil, camphorquinone, camphorquinonecarboxylic acid, 2,3-pentadione, 2,3-octadione, 9,10-phenanthrenequinone and acenaphthenequinone. Of these compounds, camphorquinone is preferable since it displays excellent curing characteristics with respect to light in a wide wavelength range.

The amount of the a-diketone phosphine compound in the dental composition is from 0.01 to 10 parts by weight, preferably from 0.05 to 5 parts by weight, and more preferably from 0.1 to 3.0 parts by weight, based on 100 parts by weight of the polymerizable monomer. When the amount of the a-diketone compound is less than 0.01 part by weight, the curing rate drastically decreases. In contrast, when the amount of the a-diketone compound is more than 10 parts by weight, the yellow color tone increases and the usable life decreases. The usable life and curing rate can be controlled by adjusting the amount of the a-diketone compound.

The polymerizable monomer used in the present invention is not restricted but it includes known monomers without limitation, and examples of monofunctional monomer compounds include ester compounds such as methyl(meth)acrylate, ethyl(meth)acrylate, methoxypolyethylene glycol (meth)acrylate, tetrafurfuryl(meth)acrylate, benzyl(meth)acrylate, phenoxyethyl(meth)acrylate, 2-hydroxyethyl(meth)acrylate, 2-hydroxypropyl(meth)acrylate, 2-hydroxybutyl(meth)acrylate, dimethylaminoethyl(meth)acrylate, 2-(meth)acryloyloxyethyl acid phosphate, etc.; styrene-based compounds such as styrene, a-mesitylene, etc.; silane compounds such as γ-(meth)acryloxypropyltrimethoxysilane, γ-(meth)acryloxypropyltriethoxysilane, etc.; nitrogen-containing compounds such as 2-(N,N-dimethylamino)ethyl(meth)acrylate and N-methylol(meth)acrylamide, etc.; fluorine-containing compounds such as trifluoroethyl(meth)acrylate, 2,2,3,3,3-pentafluoropropyl(meth)acrylate, etc.; and polymerizable silicone compounds in which the main chain of a polymer is a silicone component and one end is modified with a (meth)acrylate group.

Examples of the difunctional monomer compound include ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, 2,2-bis((meth)acryloxyphenyl)propane, 2,2-bis[4-(3-(meth)acryloxy)-2-hydroxypropoxyphenyl]propane, 2,2-bis(4-(meth)acryloxyethoxyphenyl)propane, 2,2-bis(4-(meth)acryloxydiethoxyphenyl)propane, 2,2-bis(4-(meth)acryloxytriethoxyphenyl)propane, 2,2-bis(4-(meth)acryloxytetraethoxyphenyl)propane, 2,2-bis(4-(meth)acryloxypentaethoxyphenyl)propane, 2,2-bis(4-(meth)acryloxypropoxyphenyl)propane, 2(4-(meth)acryloxydiethoxyphenyl)-2(4-(meth)acryloxydiethoxyphenyl)propane, 2(4-(meth)acryloxydiethoxyphenyl)-2(4-(meth)acryloxytriethoxyphenyl)propane, 2,2-bis(4-(meth)acryloxypropoxyphenyl)propane, 2,2-bis(4-(meth)acryloxyisopropoxyphenyl)propane, 2(4-(meth)acryloxydipropoxyphenyl)-2(4-(meth)acryloxytriethoxyphenyl)propane, etc.

Examples of the polyfunctional monomer compound having three or more polymerizable functional groups include polymerizable polyfunctional acrylates including polyethylenically unsaturated carbamoyl isocyanurate; polymerizable polyfunctional acrylates having an urethane bond, such as phenyl glycidyl ether acrylate hexamethylene diisocyanate urethane prepolymer, phenyl glycidyl ether toluene diisocyanate urethane prepolymer, pentaerythritol triacrylate toluene diisocyanate urethane prepolymer, pentaerythritol triacrylate isophorone diisocyanate urethane prepolymer, etc.; and ditrimethylolpropane tetraacrylate, ethoxylated pentaerythritol tetraacrylate, propoxylated pentaerythritol tetraacrylate, pentaerythritol tetra(meth)acrylate, dipentaerythritol tetra(meth)acrylate, dipentaerythritol penta(meth)acrylate, dipentaerythritol hexa(meth)acrylate, trimethylpropane tri(meth)acrylate, etc.

In the present invention, when only monofunctional and difunctional polymerizable monomers are used, thin-layer surface curability tends to be inferior. This problem can be solved by using a polyfunctional polymerizable monomer. The polyfunctional polymerizable monomer is preferably dipentaerythritol hexaacrylate having excellent stability, etc.

The photopolymerizable dental composition of the present invention has a problem that a cured article has a yellowish color tone. Particularly, when a (bis)acylphosphine oxide compound is used as a polymerization initiator, the cured article displays a conspicuous yellowish color tone.

Therefore, it has been found that the use of a difunctional polymerizable monomer having a molecular chain of or over a particular length is effective to suppress change in a color tone in the cured article.

That is, in the dental composition of the present invention, change in a color tone before and after curing can be decreased by containing a compound represented by the general formula (I):

[Chemical Formula 2]

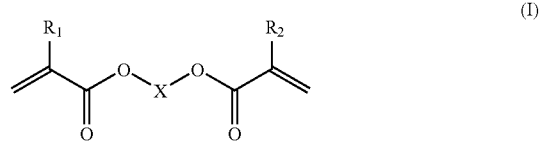

(I)

wherein $R_1$ and $R_2$ each independently represent hydrogen or a methyl group, and X represents a repeating unit composed of one or more kinds of alkylene oxide groups having 2 to 10 carbon atoms and/or derivative groups thereof and the repeating unit number is 5 to 50.

It is particularly preferable to use a compound having a repeating unit, as the X moiety, composed only of ethylene oxide groups and the repeating unit number being 9 or more. Since stiffness of the cured article deteriorates when the repeating unit number is too large, the repeating unit number is preferably from 9 to 50, and more preferably from 9 to 23.

The dental composition of the present invention may properly contain fillers depending on its purpose.

The material used as a filler includes inorganic or organic materials and composites thereof. Examples of the inorganic filler material include soda glass, lithium borosilicate glass, barium glass, strontium glass, zinc glass, fluoroaluminum borosilicate glass, borosilicate glass, crystal quartz, fused silica, synthetic silica, alumina silicate, amorphous silica, glass ceramic, and a mixture thereof, etc. There is no specific limitation on the particle size of the inorganic filler. Depending on the application of the composition, fillers having a particle diameter of several nanometers to several tens of nanometers may be selected. The inorganic filler is preferably subjected to the conventionally known surface treatment. Examples of the surface treating agent include silane compounds, for example, vinyltrimethoxysilane, vinyltriethoxysilane, vinyltrichlorosilane, vinyltri(β-methoxyethoxy)silane, γ-methacryloxypropyltrimethoxysilane, γ-glycidoxypropyltrimethoxysilane, γ-mercaptopropyltrimethoxysilane, γ-aminopropyltriethoxysilane, etc. As the organic filler, for example, polymer powders of the above polymerizable monomers, and powders (composite fillers) of composites obtained by dispersing inorganic fillers in polymerizable monomers, followed by polymerization may be used.

In addition, to the photopolymerizable dental composition of the present invention, polymerization inhibitors, ultraviolet absorbers, pigments and solvents may be added.

Examples of the polymerization inhibitor include hydroquinone, hydroquinone monomethyl ether and butylated hydroxytoluene. Among these polymerization inhibitors, hydroquinone monomethyl ether and butylated hydroxytoluene are preferable.

Examples of the solvent include water, ethanol, i-propanol, acetone, dimethyl sulfoxide, dimethylformamide, ethyl acetate, butyl acetate, etc.

The present invention relates to a photopolymerizable dental composition which is cured by irradiating with visible light, and a photopolymerization initiator used therefor, and more particularly to a dental composition which causes less change in a color tone before and after curing, and is also cured by light having a wide wavelength. The composition of the present invention is used for fillers, adhesives, surface coating materials, restorative materials for dental crowns, cements, etc.

As described above, the composition of the present invention can be applied to the field of various dental materials and is particularly suited for a low-viscosity paste-type composition since it has excellent curing characteristics when used in the form of a thin layer (thickness of 0.2 mm or less). The low-viscosity composition is operated with a hair pencil or a brush, or a probe. The most preferred composition is, as viscosity characteristics suited for the operation, thixotropic in which the viscosity is from 2 to 8 Pa·s and a ratio of a minimum value to a maximum value of the viscosity at the frequency of 7 to 1 Hz is 1.1 or more at the frequency sweep of 7 to 1 Hz measured at an initiation stress of 1.00 E+1 Pa in the measurement of the plate-on-plate viscosity at 23° C. (gap: 0.500 mm).

EXAMPLES

The present invention will now be described in detail by way of Examples and Comparative Examples. The present invention is not limited to these Examples.

Abbreviations of compounds used in Examples of the present invention are as follows.

CQ: dl-camphorquinone
APO: 2,4,6-trimethylbenzoyl-diphenylphosphine oxide
DMBE: Ethyl 4-dimethylaminobenzoate
DPH: Dipentaerythritol hexaacrylate
UDMA: Dimethacryloxyethyl-2,2,4-trimethylhexamethylene diurethane
14G: Tetradecane ethylene glycol dimethacrylate (repeating unit number n=14)
9G: Nonaethylene glycol dimethacrylate (repeating unit number n=9)
3G: Triethylene glycol dimethacrylate (repeating unit number n=3)
R-8200: AEROGIL R-8200 (manufactured by Japan Aerogil Co., Ltd.)

The procedure for evaluation of materials used in Examples of the present invention is described below.

Evaluation of Thin-Layer Surface Curability

A single drop of various photocurable compositions thus prepared was collected on a kneading paper and then spread thinly (thickness: about 0.1 mm) using a hair pencil. After irradiation with light in various photopolymerization devices, thin layer surface curability was confirmed by a hand feel. With respect to two kinds of dental light irradiators, Solidilite [manufactured by SHOFU, INC.] (irradiated for a minute) was used as a halogen lamp irradiator (Hal) and SPEKTRA LED [manufactured by Schütz Dental] (irradiated for 2 minutes) was used as an LED irradiator (LED).

A: extremely high thin-layer surface curability due to very small amount of unreacted monomer on the surface
B: high thin-layer surface curability due to small amount of unreacted monomer on the surface
C: low thin-layer surface curability due to observable amount of unreacted monomer on the surface Measurement of Color Difference Before and after Curing Each of various photocurable compositions thus prepared was placed in a stainless steel ring (inner diameter: 15 mm, thickness: 0.5 mm), followed by pressed from a vertical direction using two cover glasses and further colorimetry (L*a*b* colorimetric system) using a spectrocolorimeter CM-2002 (manufactured by Konica Minolta Photo Imaging, Inc.) to give a color tone before curing. In a photopolymerization device (Solidilite, manufactured by SHOFU, INC.), both front and back surfaces of the composition were irradiated with light each for 1 minute and then colorimetry was performed. Color differences ΔE* and Δb* before and after curing were calculated. ΔE* and Δb* are calculated as described below.

$$\Delta E^* = \sqrt{(L_x - L_y)^2 + (a_x - a_y)^2 + (b_x - b_y)^2} \quad \text{[Equation 1]}$$

$$\Delta b^* = |b_x - b_y|$$

$L_x$, $a_x$, $b_x$: Colorimetric value before curing
$L_y$, $a_y$, $b_y$: Colorimetric value after curing Measurement of Usable Life In accordance with ISO10477, using a light source in which a color temperature conversion filter is inserted into a xenon lamp, the measurement was performed in accordance with the ISO standard. On a slide glass, about 30 mg of a sample was collected and the time required to gelation of the sample under a light source was measured.

Examples and Comparative Examples of the dental composition of the present invention are shown in Table 1. The results of tests using two kinds of dental photopolymerization devices are also shown in the same table.

TABLE 1

| Components and various properties | | Examples | | | | Comparative Examples | | | | | | | |
|---|---|---|---|---|---|---|---|---|---|---|---|---|---|
| | | 1 | 2 | 3 | 4 | 1 | 2 | 3 | 4 | 5 | 6 | 7 | 8 |
| CQ (Parts by weight) | | 0.4 | 0.4 | 0.1 | 0.4 | 3 | 3 | 0.4 | — | — | 0.4 | — | — |
| APO | | 4 | 4 | 1.5 | 4 | — | — | — | 4 | 4 | — | 4 | 4 |
| MDBE | | — | — | — | — | — | 4 | — | — | 4 | 4 | — | 1 |
| DPH | | 70 | 70 | 70 | 70 | 70 | — | 70 | 70 | 70 | 70 | 100 | 70 |
| 14G | | 30 | — | 30 | — | 30 | — | 30 | 30 | 30 | 30 | — | 30 |
| 9G | | — | 30 | — | — | — | — | — | — | — | — | — | — |
| UDMA | | — | — | — | — | — | 70 | — | — | — | — | — | — |
| 3G | | — | — | — | 30 | — | 30 | — | — | — | — | — | — |
| Thin-layer surface curability | Hal | A | B | B | A | B | C | C | A | A | C | A | A |
| | LED | B | B | B | B | B | C | C | C | B | C | C | C |
| Change in color tone before and after curing | $\Delta E^*$ | 4 | 4 | 2 | 5 | 19 | 19 | 5 | 6 | 14 | 13 | 12 | 10 |
| | $\Delta b^*$ | 2 | 3 | 2 | 4 | 19 | 19 | 5 | 6 | 13 | 12 | 10 | 9 |
| Usable life (sec) | | 210 | 210 | 300 | 300 | 90 | 0 | 300 | 300 | 300 | 300 | 300 | 300 |

As is apparent from the results shown in Table 1, visible light-polymerizable dental compositions (Examples 1 to 4) which do not substantially contain an amine compound as the photosensitizer and contain 0.01 to 10 parts by weight of a (bis)acylphosphine oxide compound, 0.01 to 10 parts by weight of an α-diketone compound and a polymerizable monomer in the present invention showed excellent thin layer surface curability in both cases of using Hal and LED dental irradiators, and also showed less change in a color tone before and after curing. These compositions showed good results which satisfy ISO standard values with respect to the usable life.

The yield viscosity and the thixotropy index of a paste were measured using a Stresstech rheometer manufactured by Rheologica Instruments.

The measurement conditions are described below.
1) A plate-plate jig was set so as to adjust a distance between samples to 0.500 mm.
2) The measurement was performed under the environment of a temperature of 23° C. and an atmospheric pressure.
3) The measurement was performed at an initiation stress of 1.00 E+1 Pa.
4) The viscosity at the frequency of 10 to 1 [Hz] was measured.
5) After logarithmically plotting the frequency as the abscissas and the viscosity as the ordinate, a thixotropy ratio was obtained by dividing a maximum value of the viscosity by a minimum value. The sample where the thixotropy ratio is 1.1 or more was determined as thixotropic.

As Example 5, a composition comprising 70 parts by weight of DPH, 30 parts by weight of 14G, 4 parts by weight of APO, 0.4 part by weight of CQ and 7.5 parts by weight of R-8200 was prepared. Characteristics thereof are as shown in Table 2.

TABLE 2

| Components and various properties | DPH (Parts by weight) | 14G | APO | CQ | R-8200 | Thin-layer surface curability | | Change in color tone before and after curing | | Usable life |
|---|---|---|---|---|---|---|---|---|---|---|
| | | | | | | Hal | LED | $\Delta E^*$ | $\Delta b^*$ | |
| Example 5 | 70 | 30 | 4 | 0.4 | 7.5 | A | B | 4 | 2 | 210 |

Logarithmically plotted numerical values of the measurement results of the viscosity are shown in Table 3 and a graph is shown in FIG. 1.

TABLE 3

| Frequency (Hz) | Viscosity (Pa · s) |
|---|---|
| 10 | 3.61 |
| 9.00 | 3.59 |
| 8.00 | 3.27 |
| 7.00 | 3.28 |
| 6.00 | 3.19 |
| 5.00 | 3.19 |
| 4.00 | 3.21 |
| 3.00 | 3.52 |
| 2.00 | 3.97 |
| 1.00 | 5.73 |

As is apparent from the results shown in FIG. 1, it is found that the visible light-polymerizable dental composition (Example 5) of the present invention has the thixotropic low viscosity which is excellent in application using a hair pencil or the like.

What is claimed is:

1. A visible light-polymerizable dental composition which does not substantially contain an amine compound as a photosensitizer, comprising 0.01 to 10 parts by weight of a (bis)acylphosphine oxide compound, 0.01 to 10 parts by weight of an α-diketone compound and 100 parts by weight of dipentaerythritol hexaacrylate as a polymerizable monomer.

2. The visible light-polymerizable dental composition according to claim 1, wherein the (bis)acylphosphine oxide compound is 2,4,6-trimethylbenzoyldiphenylphosphine oxide.

3. The visible light-polymerizable dental composition according to claim 1, wherein the α-diketone compound is camphorquinone.

4. The visible light-polymerizable dental composition according to claim 1, which further comprises a polymerizable monomer represented by the general formula (I):

[Chemical Formula 1]

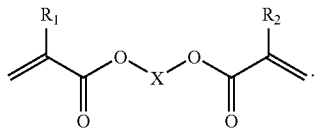

(I)

wherein $R_1$ and $R_2$ each independently represent hydrogen or a methyl group, and X represents a repeating unit composed of one or more kinds of alkylene oxide groups having 2 to 10 carbon atoms and/or derivative groups thereof and the repeating unit number n=5 to 50.

5. The visible light-polymerizable dental composition according to claim 4, wherein X in the general formula (I) is a repeating unit composed only of an ethylene oxide group and the repeating unit number n=9 to 23.

6. The visible light-polymerizable dental composition according to claim 4, which contains the polymerizable monomer represented by the general formula (I) in the amount of 5 to 90 parts by weight based on the entire amount of the polymerizable monomer.

7. The visible light-polymerizable dental composition according to claim 1, which further contains 0.1 to 90 parts by weight of at least one kind of an inorganic or organic filler.

8. The visible light-polymerizable dental composition according to claim 1, which is thixotropic in that a ratio of a minimum value to a maximum value of the viscosity at the frequency of 7 to 1 Hz is 1.1 or more and the viscosity takes a value from 2 to 8 Pa·s at a frequency sweep of 7 to 1 Hz measured at an initial stress of 1.00E+1 Pa in the measurement of the plate-on-plate viscosity at 23° C. (gap: 0.500 mm).

9. The visible light-polymerizable dental composition according to claim 2, wherein the α-diketone compound is camphorquinone.

10. The visible light-polymerizable dental composition according to claim 2, which further comprises a polymerizable monomer represented by the general formula (I):

[Chemical Formula 1]

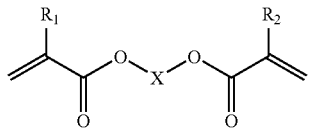

(I)

wherein $R_1$ and $R_2$ each independently represent hydrogen or a methyl group, and X represents a repeating unit composed of one or more kinds of alkylene oxide groups having 2 to 10 carbon atoms and/or derivative groups thereof and the repeating unit number n=5 to 50.

11. The visible light-polymerizable dental composition according to claim 3, which further comprises a polymerizable monomer represented by the general formula (I):

[Chemical Formula 1]

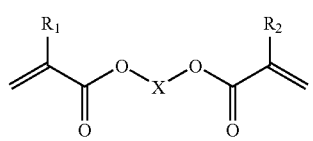

(I)

wherein $R_1$ and $R_2$ each independently represent hydrogen or a methyl group, and X represents a repeating unit composed of one or more kinds of alkylene oxide groups having 2 to 10 carbon atoms and/or derivative groups thereof and the repeating unit number n=5 to 50.

12. The visible light-polymerizable dental composition according to claim 5, which contains the polymerizable monomer represented by the general formula (I) in the amount of 5 to 90 parts by weight based on the entire amount of the polymerizable monomer.

13. The visible light-polymerizable dental composition according to claim 2, which further contains 0.1 to 90 parts by weight of at least one kind of an inorganic or organic filler.

14. The visible light-polymerizable dental composition according to claim 3, which further contains 0.1 to 90 parts by weight of at least one kind of an inorganic or organic filler.

15. The visible light-polymerizable dental composition according to claim 4, which further contains 0.1 to 90 parts by weight of at least one kind of an inorganic or organic filler.

16. The visible light-polymerizable dental composition according to claim 5, which further contains 0.1 to 90 parts by weight of at least one kind of an inorganic or organic filler.

17. The visible light-polymerizable dental composition according to claim 6, which further contains 0.1 to 90 parts by weight of at least one kind of an inorganic or organic filler.

18. The visible light-polymerizable dental composition according to claim 2, which is thixotropic in that a ratio of a minimum value to a maximum value of the viscosity at the frequency of 7 to 1 Hz is 1.1 or more and the viscosity takes a value from 2 to 8 Pa·s at a frequency sweep of 7 to 1 Hz measured at an initial stress of 1.00E+1 Pa in the measurement of the plate-on-plate viscosity at 23° C. (gap: 0.500 mm).

19. The visible light-polymerizable dental composition according to claim 3, which is thixotropic in that a ratio of a minimum value to a maximum value of the viscosity at the frequency of 7 to 1 Hz is 1.1 or more and the viscosity takes a value from 2 to 8 Pa·s at a frequency sweep of 7 to 1 Hz measured at an initial stress of 1.00E+1 Pa in the measurement of the plate-on-plate viscosity at 23° C. (gap: 0.500 mm).

20. The visible light-polymerizable dental composition according to claim 4, which is thixotropic in that a ratio of a minimum value to a maximum value of the viscosity at the frequency of 7 to 1 Hz is 1.1 or more and the viscosity takes a value from 2 to 8 Pa·s at a frequency sweep of 7 to 1 Hz measured at an initial stress of 1.00E+1 Pa in the measurement of the plate-on-plate viscosity at 23° C. (gap: 0.500 mm).

21. The visible light-polymerizable dental composition according to claim 5, which is thixotropic in that a ratio of a minimum value to a maximum value of the viscosity at the frequency of 7 to 1 Hz is 1.1 or more and the viscosity takes a value from 2 to 8 Pa·s at a frequency sweep of 7 to 1 Hz measured at an initial stress of 1.00E+1 Pa in the measurement of the plate-on-plate viscosity at 23° C. (gap: 0.500 mm).

22. The visible light-polymerizable dental composition according to claim 6, which is thixotropic in that a ratio of a minimum value to a maximum value of the viscosity at the frequency of 7 to 1 Hz is 1.1 or more and the viscosity takes a value from 2 to 8 Pa·s at a frequency sweep of 7 to 1 Hz measured at an initial stress of 1.00E+1 Pa in the measurement of the plate-on-plate viscosity at 23° C. (gap: 0.500 mm).

23. The visible light-polymerizable dental composition according to claim 7, which is thixotropic in that a ratio of a minimum value to a maximum value of the viscosity at the frequency of 7 to 1 Hz is 1.1 or more and the viscosity takes a value from 2 to 8 Pa·s at a frequency sweep of 7 to 1 Hz measured at an initial stress of 1.00E+1 Pa in the measurement of the plate-on-plate viscosity at 23° C. (gap: 0.500 mm).

* * * * *